United States Patent [19]
Kennedy

[11] Patent Number: 6,071,247
[45] Date of Patent: Jun. 6, 2000

[54] SKIN BLISTER BIOPSY APPARATUS AND METHOD

[76] Inventor: William R. Kennedy, 2259 Summit Ave., St. Paul, Minn. 55105

[21] Appl. No.: 08/903,948

[22] Filed: Jul. 31, 1997

Related U.S. Application Data

[60] Provisional application No. 60/022,849, Jul. 31, 1996.

[51] Int. Cl.⁷ ..................................... A61B 10/00
[52] U.S. Cl. .......................... 600/562; 128/898; 604/290; 604/313
[58] Field of Search ............................ 600/562; 604/289, 604/290, 313; 623/15; 128/897, 898

[56] References Cited

U.S. PATENT DOCUMENTS

| | | | |
|---|---|---|---|
| 2,590,299 | 3/1952 | Douglas | 128/305 |
| 4,026,091 | 5/1977 | Pearson | 53/390 |
| 4,844,098 | 7/1989 | Mitchen | 600/578 |
| 5,441,490 | 8/1995 | Svedman . | |
| 5,492,465 | 2/1996 | Matuzawa et al. | 425/214 |
| 5,885,211 | 3/1999 | Eppstein et al. | 600/309 |

OTHER PUBLICATIONS

Kiistala et al., "Dermo–epidermal separation with suction. Electron microscopic and histochemical study of initial events of blistering in human skin." J Invest Derm 48:466–478, 1967.

Kiistala et al., "Suction blister device for separation of viable epidermis for dermis." J Invest Derm 50:129–135, 1968.

Boyd et al., "Scanning electron microscopy of the basal surface of the separated suction blister top. " Br J Derm 84:346–352, 1971.

Peachey, R.D.G., "Some factors affecting the speed of suction blister formation in normal subjects." Br J Derm 84:435–446, 1971.

Peachey, R.D.G., "Skin temperature and blood flow in relation to the speed of suction blister formation." Br J Drm 84:447–452, 1971.

Kiistala, U., "Dermal–Epidermal Separation. The influence of age, sex, and body region on suction blister formation in human skin." Ann Clin Res 4:10–22, 1972.

Kiistala, U., "Dermal–Epidermal Separation. II. External factors in suction blister formation with special reference to the effect of temperature." Ann Clin Res 4:236–246, 1972.

Beerens et al., "Rapid Regeneration of the dermal–epidermal junction after partial separation by vacuum: an electron microscopic study." J Invest Derm 65:513–521, 1975.

Lindberger et al., "Nerve fibre studies in skin biopsies in peripheral neuropathies.I. Immunohistochemical analysis of neuropepetides in diabetes mellitus." J Neurol Sci 93:289–296, 1989.

Deleuran et al., "Increased tryptase levels in suction–blister fluid from patients with urticaria" Br j Derm 125:14–17, 1991.

Rommain et al., "A skin suction blister model in hairless rats: Application to the study of anti–inflammatory and immunomodulatory drugs." Int. J Innunopharmac 13:379–384, 1991.

(List continued on next page.)

*Primary Examiner*—Cary O'Connor
*Assistant Examiner*—Charles Marmor, II
*Attorney, Agent, or Firm*—Skinner and Associates

[57] ABSTRACT

A skin blister method and apparatus are disclosed to evaluate and quantify epidermal nerves by separating an epidermis sample. The method is useful for a variety of purposes including diagnosis of neuropathy or nerve injury from any cause; measurement of the time course and character of nerve regeneration with and without modifying influences; and measurement of the response of normal, abnormal or regenerating nerves to exposure to various types of chemical or physical modalities. The principle step in the process of the invention is the creation of a skin blister, preferably by means of negative pressure. The blister consists of the epidermis, its nerves and fluid. The epidermis is subsequently studied by one or more of a variety of processes. The apparatus of the invention comprises a capsule with a chamber which is connected to a gage, pump and connecting valves.

22 Claims, 7 Drawing Sheets

(7 of 7 Drawing Sheet(s) Filed in Color)

OTHER PUBLICATIONS

Svedman et al., "Epithelialization and blood flow in suction blister wounds on healthy volunteers." J Invest Surg 4:175–189, 1991.

Terenghi et al., "Image analysis quantification of peptide–immunoreactive nerves in the skin of patients with raynaud's phenomenon and systemic sclerosis." J Pathol 164:245–252, 1991.

Treffel et al., "Citropten and Bergapten suction blister fluid concentrations after solar product application in man." Skin Pharmac 4:100–108, 1991.

Alanko et al., "Suction blister fluid histamine infixed drug eruption." Acta Dermato–Venereologica, 72:89–91, 1992.

Levy et al., "Immunohistochemical measurements of nerves and neuropeptides in diabetic skin: relationship to tests of neurological function." Diabetologia 35:339–897, 1992.

Lundin et al., "Topical retinois acid treatment of photoaaged skin: Its effects on hyaluronan distribution in epidermis and on hyaluronan and retinoic acid in suction blister fluid." Acta Dermato–Venereologica 72:432–437, 1992.

Molina et al., "Increased sensory neuropeptides in nodular prurigo: a quantitative immunohistochemical analysis." Br J Dermatol 127:344–351, 1992.

Kennedy et al., "The innervation of human epidermis." J Neurol Sci 115:184–190, 1993.

Properzi et al., "Early increase precedes a depletion of VIP and PGP–9.5 in the skin of insulin–dependent diabetic–correlation between quantitative immunohistochemistry and clinical assessment of peripheral neuropathy." J Path 169:269–277, 1993.

Schopf et al., "Soluble CD14 Monocyte Antigen in Suction Blister Fluid and Serum of Patients with Psoriasis." Dermatology 186(1) 45–49, 1993.

Westerman et al., "The role of skin nociceptive afferent nerves in blister healing." Clin Exp neurol 30:39–69, 1993.

Kennedy et al., "Diagnostic skin biopsy in peripheral nerve disease." Peripheral Nerve Society annual meeting St. Paul, MN. Jun. 14, 1994.

Kennedy et al., "Quantification of Nerve in Skin Biopsies from Control and Diabetic Subjects." Presented at the annual meeting of the American Academy of Neurology, Washington, D.C., May 3, 1994. Neurology 44 (suppl 2) :A275, 1994.

Kennedy et al., "Usefulness of skin biopsy as a diagnostic procedure for quantitative assessment of neuropathic disease." VIII. International Congress on Neuromuscular Diseases, Kyoto, Japan, Jul. 10–15. Muscle & Nerve Suppl.1, S 252, 1994.

Kennedy et al., "A quantitative skin biopsy study of epidermal nerves in normal and diabetic subjects." Peripheral Nerve Society meeting. Antalya, Turkey, Oct. 9, 1995.

Kennedy et al., "Quantitation of epidermal nerves in diabetic neuropathy." Neurology 1996. In Press Nov. 1995.

Kennedy et al., "Assessment of diabetic neuropathy by quantitation of nerves in human skin biopsy." Society for Neuroscience Meeting, Sand Diego, CA, Nov. 15, 1995.

McCarthy et al., "Cutaneous innervation in sensory neuropathies: Evaluation by skin biopsy." Neurology 45:1848–1855, 1995.

Langlois et al., "Non–enzymatic Retrieval of antigen Permits Staining of Follicle Centre Cells by the Rabbit Polyclonal Antibody to Protein Gen Product 9.5", Journal of Pathology, 1994; vol. 172: 249–253.

McQuaid et al., "Microwave Antigen Retrieval for Immunocytochemistry on Formalin–Fixed, Paraffin–Embedded Post–Morten CNS Tissue", Journal of Pathology, 1995; vol. 176: 207–216.

SKIN BLISTER BIOPSY APPARATUS AND METHOD

CROSS-REFERENCE TO RELATED APPLICATIONS

This application claims the benefit under 35 U.S.C. §119 (e) of co-pending provisional application Ser. No. 60/022, 849, filed Jul. 31, 1196 application Ser. No. 60/022,849, is hereby incorporated by reference.

STATEMENT REGARDING FEDERALLY SPONSORED RESEARCH OR DEVELOPMENT

This invention was made with government support under NIH Grant No. NS-31397.

REFERENCE TO A MICROFICHE APPENDIX

Not Applicable.

BACKGROUND OF THE INVENTION

1. Field of the Invention.

The present invention relates, generally, to medical methods and devices. More particularly, the invention relates to a method to isolate, image, evaluate and quantify cutaneous nerves for establishing a diagnosis, for studying nerve regeneration and/or for measuring response to treatment. The invention has particular utility in neurology for diagnosis of diabetic neuropathy and other disorders of peripheral nerves; and in dermatology; immunology and wound healing. The invention is also useful for investigators doing research on cutaneous nerves. The invention is further useful for pharmaceutical industry to determine the effect of a new drug on wound healing or on the cutaneous nerves.

2. Background Information.

In the past, various devices and methods have been used or proposed in the diagnosis of nerve abnormalities in the dermis including nerve biopsy and skin biopsy. Nerve biopsy has been judged as unacceptable for many uses. It requires a long incision and there is a possibility of infection. It leaves the patient with a permanent sensory loss on the ankle and foot. The same area is susceptible to future infection (especially if a diabetic patient) and dysesthesias (spontaneous pains in the skin). The information obtained is often not directly related to the patient's problem. Skin biopsy is a new procedure and although promising is as yet untested. Insofar as is known, no one has isolated epidermal nerves by separating and removing an epidermis sample, particularly using a skin blister technique, for the purposes discussed above, either alone or in combination with skin biopsy.

Several publications report on making the skin blister. The first was by Kiistala in 1964. Most of the work on the blisters has been on the regrowth of the epidermis, changes in the capillaries, and chemical and cell composition of the blister fluid. None of the work has involved the nerves in the epidermis and none have involved studies of the effects of drugs on the nerves in the roof of the blister. One study looked at the nerves in the underlying dermis in wound healing after blister formation and one studied the role of cutaneous nerves in wound healing.

Despite the need to isolate epidermal nerves by a skin blister method for the purpose of evaluating and quantifying the epidermal nerves which overcomes the disadvantages, shortcomings and limitations of the prior art, none insofar as is known has been developed. Accordingly, it is an object of the present invention to provide an improved method and apparatus which overcome the limitations and shortcomings of the prior art.

BRIEF SUMMARY OF THE INVENTION

The present invention provides an apparatus and method to biopsy and quantify nerves in human or animal skin. A skin blister is created by applying approximately 100 to 600 mm Hg negative pressure. Blister development can be accelerated by increasing pressure, temperature and subject age. The skin separation point is usually just above or at the dermato-epidermal basement membrane. Capillaries usually remain structurally intact. The blister consisting of epidermis and epidermal nerves is removed, stained (usually by immunohistochemistry) for nerve or contents of the epidermal intra- or inter cellular contents or other characteristics, imaged and subjected to computer analysis for number of nerves, nerve length and nerve branching (or other substances) per epidermal surface area and volume. If the blister roof is left on the skin most of the old epidermis and all nerves in the roof degenerate. New epidermis is formed in a few days and new nerves begin to appear within a week. The new epidermis can be analyzed for nerves by forming another blister over the first blister (reblister) and removing the blister roof. The nerve number, length and branching in the new epidermis may be analyzed. This analysis can be made visually, for example, by morphometric analysis of analogue microscopic images, from digital images made by confocal or 2-photon microscopy, or by chemical analysis. The method can be used to evaluate the regeneration of new epidermis, new epidermal nerves growth or the reaction of the underlying tissue to the procedure.

Regeneration can be accomplished by direct viewing of the tissue in vivo or by making a second blister at the same site at a later time to evaluate the speed of regeneration, or by taking a full thickness skin biopsy. Furthermore, substances thought to accelerate delay or otherwise influnce regeneration of the nerves or epidermis or underlying tissue can be placed into or near the blister or directly on the blister cavity floor, after the roof of the blister has been removed and the effect evaluated as above. Examples of compounds that can be tested include but are not limited to trophic substances to improve neuropathy or nerve damage of any type, and compounds suspected to have toxic effects on nerve, epidermis, capillaries or basement membrane or wound healing, but that may be beneficial in cancer therapy. The patient can serve as his/her control if some (or multiple) sites contain the tested substance(s) and others are without.

The features, benefits and objects of this invention will become clear to those skilled in the art by reference to the following description and drawings.

BRIEF DESCRIPTION OF THE SEVERAL VIEWS OF THE DRAWING

The file of this patent contains at least one drawing executed in color. Copies of this patent with color drawing (s) will be provided by the Patent and Tradmark Office upon request and payment of the necessary fee.

DETAILED DESCRIPTION

1. Overview of the Method of the Invention.

The present invention provides a method to biopsy and quantify nerves in human or animal skin by isolating epidermal nerves. The figures illustrate a method for isolating epidermal nerves by forming a blister to separate an epidermis sample. Other methods for isolating epidermal nerves by separating an epidermis sample include soaking the skin in salt solutions or passing loosening substances through the skin. Referring to the specific method shown in the figures, the first step in the illustrated process, is creation of a skin blister, preferably by means of negative pressure approximately 100–600 mm Hg. Basically, this involves placing a suction capsule a predetermined skin site. The suction capsule is preferably held in place by adhesive tape, a strap, and/or an elastic bandage. A tube is connected to the suction capsule and to a pump, which is then actuated to apply a predetermined negative pressure or suction. Upon attaining necessary suction, the tube may be clamped off or the pressure may be monitored by a gage to assure maintenance of pressure. The pump may be activated by the subject to compensate for any pressure fluctuation. The blister forms more rapidly with increasing negative pressure and increasing skin temperature, therefore a heating pad is preferably applied to the area. The suction capsule preferably contains a plate with one to several holes of different size against the skin surface to form blisters of different size. The skin is drawn into the holes to create a blister of the desired size. The blister consists of the surface layer of skin, called the epidermis, its nerves and fluid. After a predetermined time period, the heating pad, holder, and suction capsule are removed to expose the blister. The blister is then carefully removed for example by scissors. The blister is then analyzed by one of the methods discussed below.

Figure 8:
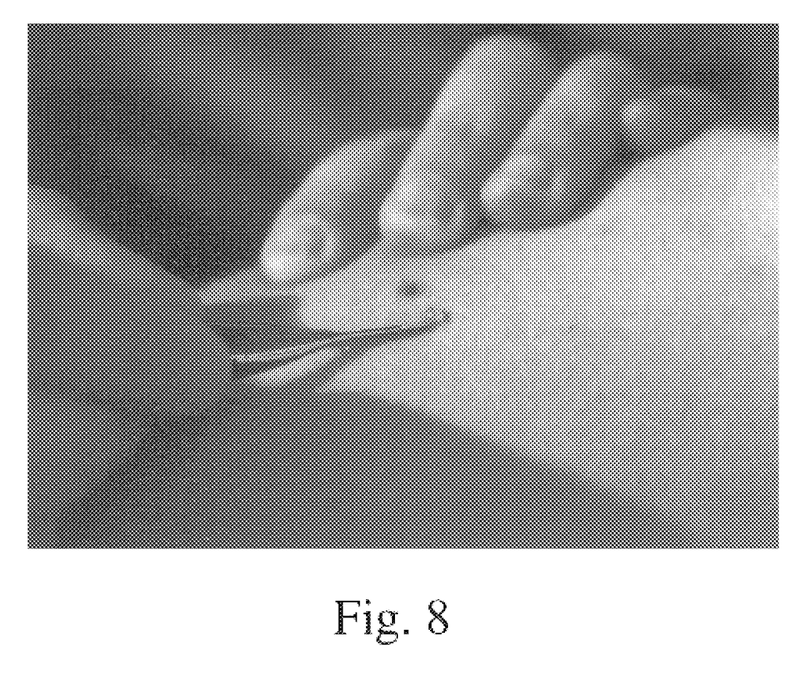
FIG. 8 shows a blister being removed via scissors for later analysis, and further shows a second blister site wherein the blister has already been removed to expose the capillary loops and wherein there is no bleeding at the site.
Figure 9:
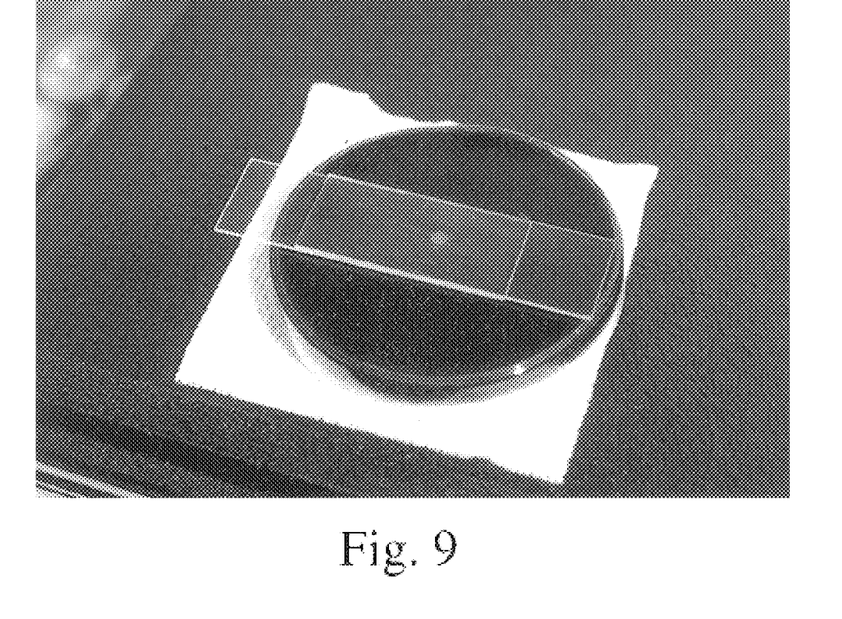
FIG. 9 shows the removed blister roof in place on a microscope slide for subsequent staining.
Figure 10:
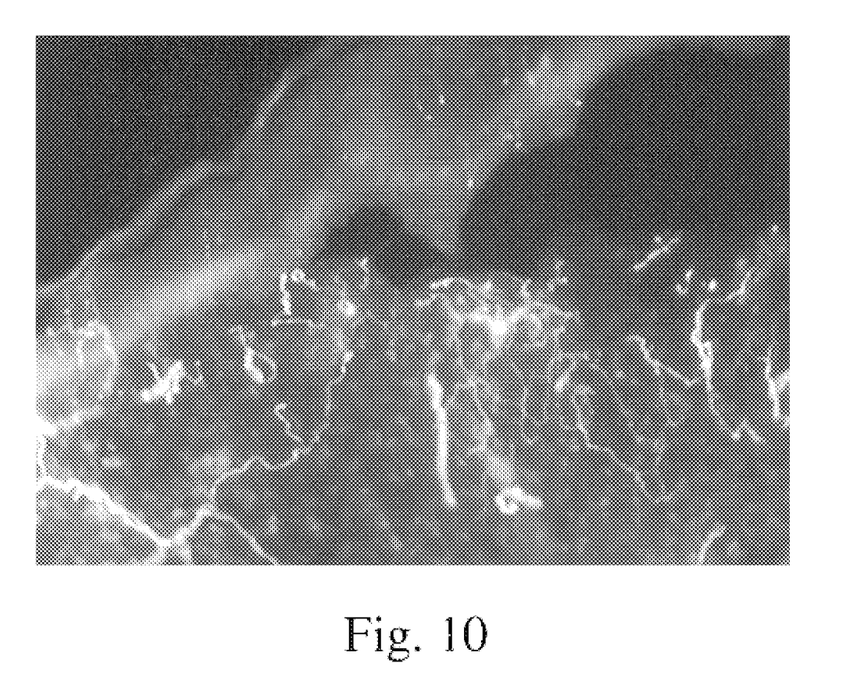
FIG. 10 shows the skin biopsy stained by immunoreaction with antibody to protein gene product 9.5 and a secondary antibody that has conjugated with a fluorescent compound cyanine 3.18, then viewed in a fluorescent microscope; the skin biopsy being taken in crossection through one edge of a blister; blister roof (epidermis) being at the top and showing the nerves, intact skin being at the left and a thick nerve in base dermis extending toward the epidermis, a stump of nerves that were ruptured being in the center and right below the dark cavity under the blister roof
Figure 11:
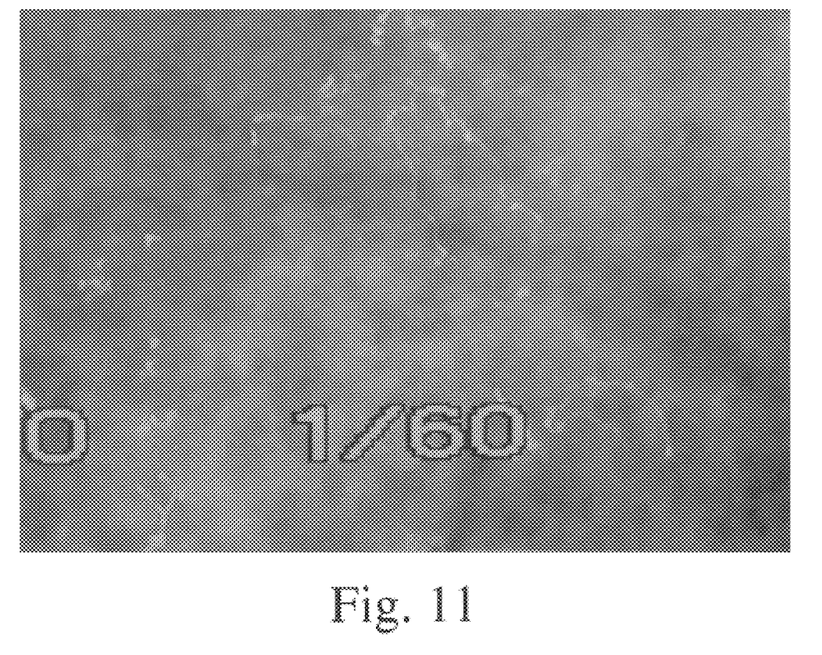
FIG. 11 is a view from the top of the separated and stained blister roof and showing nerves (white).
Figure 12:
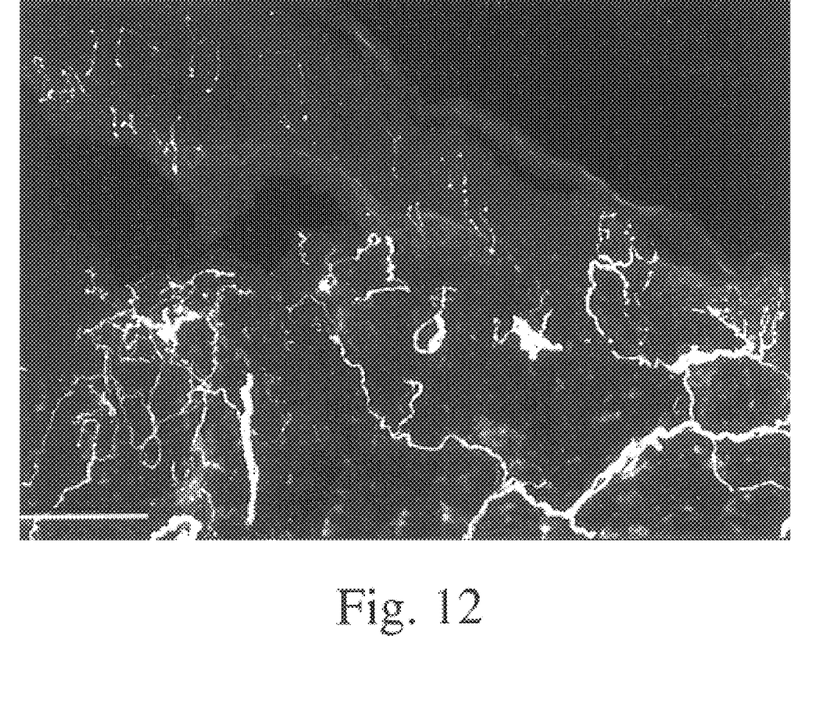
FIG. 12 is a view through a laser scanning confocal microscope (LSCM) of the blister roof shown in FIG. 11, reversed and showing nerves in the blister roof in detail.
Figure 13:
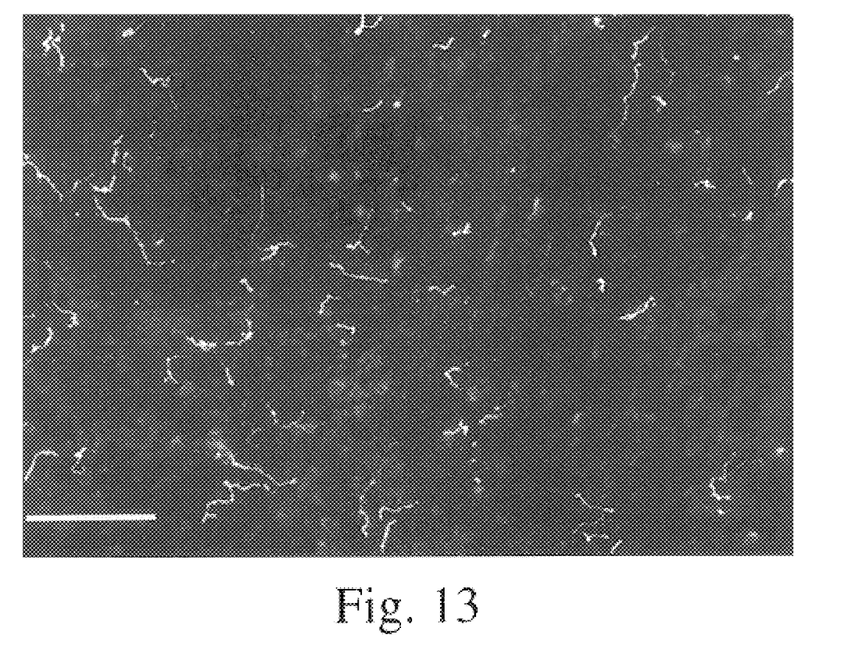
FIG. 13 is view of the blister roof through an LSCM showing fine epidermal nerve fibers in the roof.

Referring to FIGS. 8–13, human skin contains epidermal nerve fibers in large numbers. The roof of the blister contains the epidermal nerve fibers which are separated from their origins by the negative pressure. The separation point between the epidermis and underlying dermis is just above or at the dermal-epidermal basement membrane. Small amounts of basement membrane sometimes remain adherent to the blister roof, and some epidermal keratinocyte cells sometimes remain adherent to the basement membrane on the blister floor. Skin capillaries deep to the basement membrane remain intact, except for occasional inclusion of a capillary loop in the blister roof. Since the epidermal nerves are now separated from their central connections the blister roof can be painlessly removed from the underlying skin, preferably by sharp scissors, and stored for later processing or chemical analysis.

The blister permits diagnosis and evaluation of treatment for peripheral nerves. A laser scanning confocal microscope is preferably used to describe the number, length, and branching of epidermal nerves. The blister roof contains only epidermal nerves uncontaminated by other nerves. The nerves can be counted, measured for volume or surface area and branching. The roof can be analyzed chemically for the contents of these nerves without fear of contamination by other nerves. The method permits viewing of the nerves in the epidermis, their reaction to blister formation or to the addition of substances. The method permits evaluation of epidermal nerves that are not easily seen by other methods and there are 10 to 25 times the number of epidermal nerves in one blister as can be seen in one skin biopsy section. This helps solve the sampling error of the prior art typical 2 to 3 mm skin biopsy site.

Another benefit is in improved reinnervation studies. After creation of a suction blister, the nerves in the blister roof can be stained and quantified, either for diagnosis or evaluation of the results of a therapeutic clinical trial for increasing the number or length of epidermal nerves. The blister separates the epidermal nerves from their roots in the dermis. Therefore follow-up studies may be done to determine the success of reinnervation of the blister and whether any substances put into the blister help reinnervation. For reinnervation a first blister pulls the epidermal nerves off the dermis with the epidermis, then after a delay of days to weeks a second blister is made to see the regenerated nerves in the new, regenerated epidermis. Therapeutic substances like nerve growth substance can be put into the blister to see its effect on regeneration.

Some of the advantages are that the process is painless, bloodless and therefore innocuous; fast; inexpensive to perform; patient recovery is fast and it leaves little to no detectable scar or sensory defect; it can be done simultaneously on several sites and repeated if needed; and when used for diagnosis or to determine the effects of applied substances (therapy) on nerves, the results are quantitative and the amount of therapy (chemical or physical) necessary is correspondingly many times smaller and correspondingly less toxic to the subject. The nerves are processed rapidly and inexpensively. Quantitation may be accomplished via a laser scanning confocal microscope or fluorescent microscope, collected in digital form via a frame grabber and counted by software means.

2. Uses of the Method.

The method is useful for a variety of purposes including diagnosis of neuropathy or nerve injury from any cause; measurement of the time course and character of nerve regeneration with and without modifying influences; and measurement of the response of normal, abnormal or regenerating nerves to exposure to various types of chemical or physical modalities. Specific uses are set forth as follows.

A. Diagnosis of Nerve Injury and Neuropathy.

A first use is in the diagnosis of nerve injury and neuropathy. Diabetes mellitus, and some other diseases, cause degeneration of peripheral nerves to skin, muscle, bowel and other organs (called neuropathy). If diagnosed early the treatment is more rigorous. The invention would help in the diagnosis in a patient suspected of having neuropathy, or as a screening for neuropathy in a larger population.

The removed blister roof, consisting of epidermis and epidermal nerves can be stained (usually by immunohistochemistry) imaged and subjected to computer analysis (with appropriate software) for number of nerve fiber fragments, nerve length and nerve branching per epidermal surface area and volume. If biopsies from the same skin site of normal subjects have been quantified it is possible to diagnose a loss of number or change in structural character of nerves, determination of intra- or inter cellular constituents or fluids of the epidermis and other characteristics. In the presence of a neuropathy (e.g. diabetic neuropathy) the analysis will demonstrate abnormal results and establish the diagnosis.

Nerve injury, intrinsic as from a herniated disk or extrinsic as in industrial accidents, will also result in abnormalities such as decreased nerve number or nerve absence. Because of the innocuous nature of the procedure, blisters can be made at multiple strategic skin sites to improve sampling and to distinguish between a generalized nerve disorder and a local nerve injury. The importance of this method is better appreciated when it is realized that nerve biopsy (almost always the sural nerve) is the only other method used to evaluate peripheral nerve structure. Nerve biopsy requires an incision and is subject to infection, scar formation, painful sensations after healing and sensory loss in the skin territory of the biopsied nerve. To evaluate a mode of therapy the process must be repeated before and after treatment. There are only two sural nerves, one at each ankle. When these are used the patient is excluded from additional treatment trials.

B. Evaluation of Nerve Regeneration.

A second use is for evaluation of nerve regeneration. If a blister is made and left undisturbed, the old epidermis in the blister roof and the nerves in the roof degenerate. Within a week new nerve sprouts begin to grow from the severed nerves in the base of the blister and from more normal nerves surrounding the blister, and grow into newly regenerated epidermis, the number increasing daily. The new nerve terminals can be analyzed by repeating the blister formation procedure at the same location and analyzing the nerves as above in #I. The bed of the blister can also be flooded with a vital dye that stains living nerves and the progress of regeneration observed continuously. There are currently no other methods existing to measure rate of growth and quality and quantity of regenerating nerves in terms of days in animals or humans. The regeneration of nerves could be done at even earlier stages of trauma by making partial blisters with partial denervation of the epidermis. This lesion is not as predictable in degree as a complete blister.

This invention gives investigators or pharmaceutical companies a method to evaluate drugs, synthetic or natural compounds or physical entities (e.g. electric current) that are thought to accelerate nerve growth (or otherwise aid in the treatment of neuropathic conditions). The therapy can be placed inside the original blister compartment or on the floor of compartments that have had the roof removed, or under an artificial roof (like a glass or plastic dome), either in solution, as crystals or adsorbed on synthetic materials for slow release. Examples of compounds that can be tested include, but are not limited to, trophic substances to improve neuropathy or nerve damage of any type, or compounds suspected to have toxic effects on nerve, epidermis, capillaries or basement membrane or wound healing. Sometimes compounds that have beneficial effects on other tissues, such as in treatment of cancer, are toxic to nerves, epidermis or capillaries. All of the above can be tested in small doses on animals or humans to learn of their effects. The patient is the control if the tested substance is in one blister and the vehicle in another blister. The method has potential for shortening the evaluation time for new drugs. Use of the blister "chamber" to study regeneration is also important for studying the basic principals of nerve regeneration and degeneration. Combination of the blister method with the skin biopsy method (that includes dermal nerves) of measuring epidermal nerve content can add to knowledge gained about nerve regeneration.

C. Monitoring of Epidermal Regeneration and the Effects of Certain Compounds.

A third use is to monitor the regeneration of new epidermis and the effects of chemical compounds, natural or synthetic on the process. New epidermis is formed in a few days. This can be monitored at first by staining the new epidermis in situ and watching it grow toward the center from the edges. The thickness can be measured by small skin biopsy, or by formation of a new blister and measurement in the confocal microscope. The process of blister formation can be repeated at the same location and reanalyzed. Cells in epidermis manufacture epidermal growth substance, nerve growth factor and other peptides that can be sampled from blisters to determine the time course of manufacture and other parameters.

D. Therapy.

A fourth use is of the blister roof and blister fluid as therapeutic agents. Therapeutic agents may be applied either systemically or locally. The process of epidermal nerve regeneration takes more time when the roof is removed or merely opened and the fluid escapes then if left undisturbed. This implies that the old epidermis and/or the blister fluid contain substances that are important for healing. Tissue fluid is obtained for analysis of the cellular and chemical contents of blister fluid and to test them for their ability to improve epidermal nerve regeneration, epidermis regeneration and reactivity of the capillary bed Prior art methods to evaluate response to therapy are morphological (nerve biopsy), physiological (nerve conduction, sensory examination etc.) and functional (return of strength, time to walk a measured distance etc.). All are satisfactory to a limited degree, but are not exacting enough to detect small benefits as is evidenced by the search for more quantitative methods by the pharmaceutical industry. Few exist to evaluate nerve function except, sensory examination for ability to feel touch, pain, heat, cold, sweating capability and skin flare response to histamine etc.

E. Monitoring Changes in Capillary Bed of Dermis For Wound Healing.

A fifth use is to monitor changes in the capillary bed of the dermis. After the blister roof is removed, if the base of the blister is microscopically examined one can see the capillary bed and capillary loops. The capillaries react by proliferating, nearby nerves elaborate new growth cones that will elongate and pass into the newly constituted epidermis. The reaction of the base to blister formation can be monitored over time and the influence of naturally occurring or manufactured substances on the process can be measured. This knowledge gained is of great importance to hastening healing of lacerations, burns and other wounds.

3. Overview of the Apparatus of the Invention.

Figure 1:
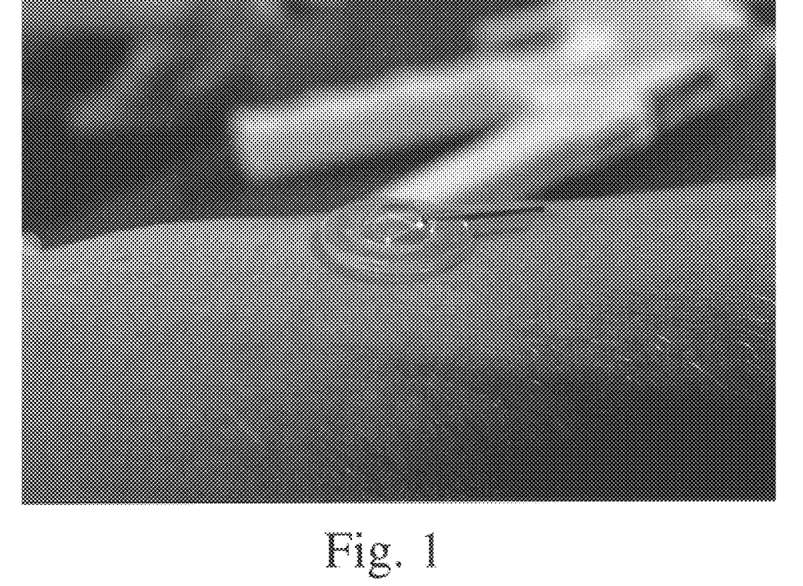
FIG. 1 illustrates the placement of a capsule assembly on the skin of a patient at a site selected for blister creation.
Figure 2:
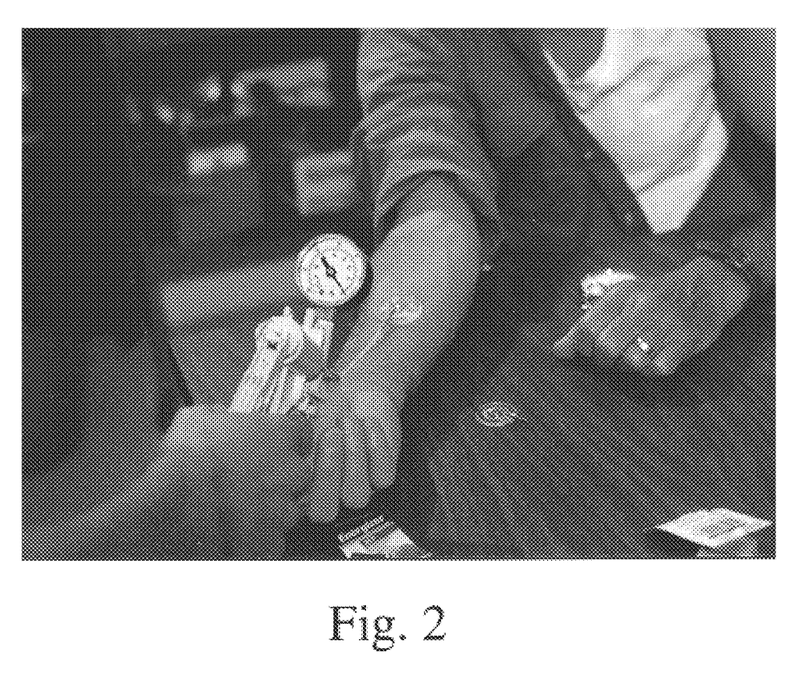
FIG. 2 illustrates the connection of a pump assembly to the capsule assembly shown in FIG. 1 and actuation of the pump to create a vacuum in the capsule to approximately 200–300 mm Hg. Several varieties of gauges and pumps, including simple hand pumps and more complex powered pumps, may be used.
Figure 3:
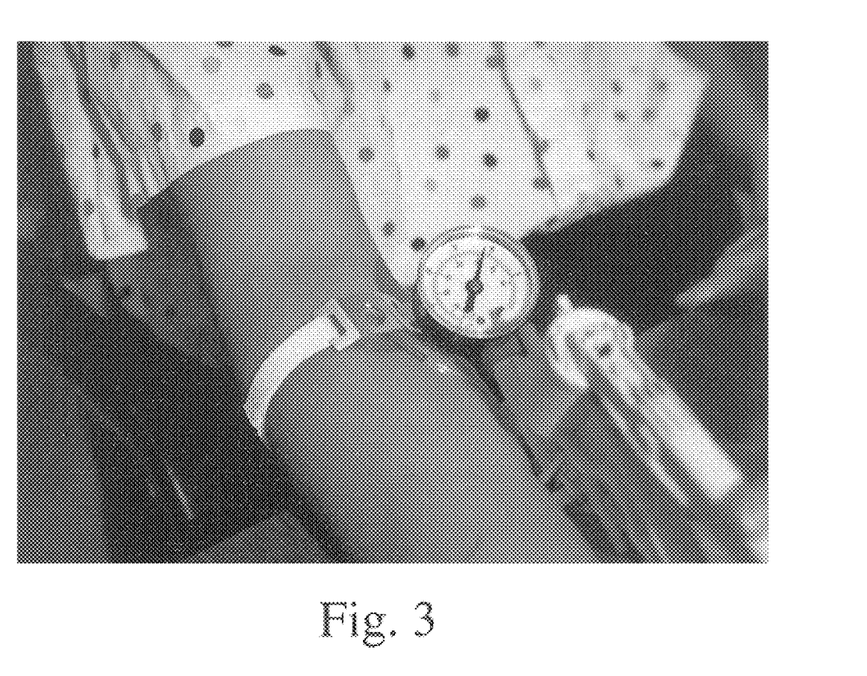
FIG. 3 shows an alternative capsule placement on the skin wherein a strap is used to hold the capsule in place.
Figure 4:
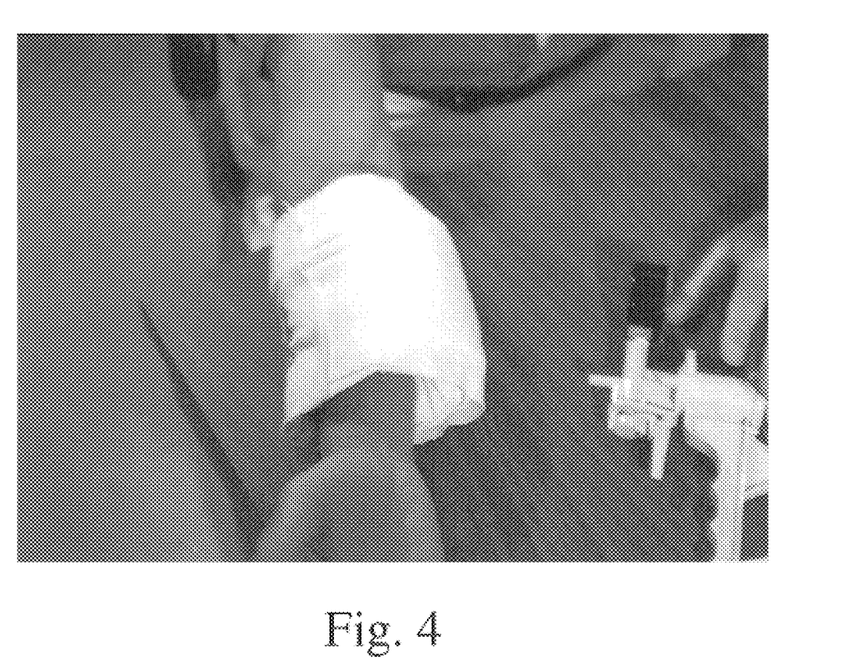
FIG. 4 illustrates the optional placement of a heating pad over an elastic bandage, which is itself applied over the sealed capsule applied to the skin. heating may also be provided by an electrical heating plate disposed in the capsule.
Figure 5:
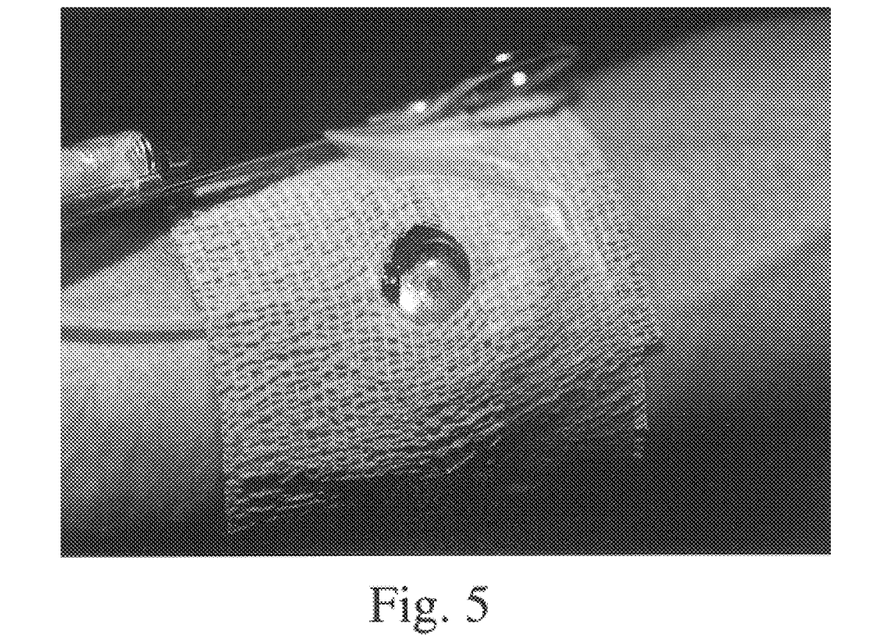
FIG. 5 shows a hole cut in the elastic bandage to view the blister formed under the clear capsule body.
Figure 6:
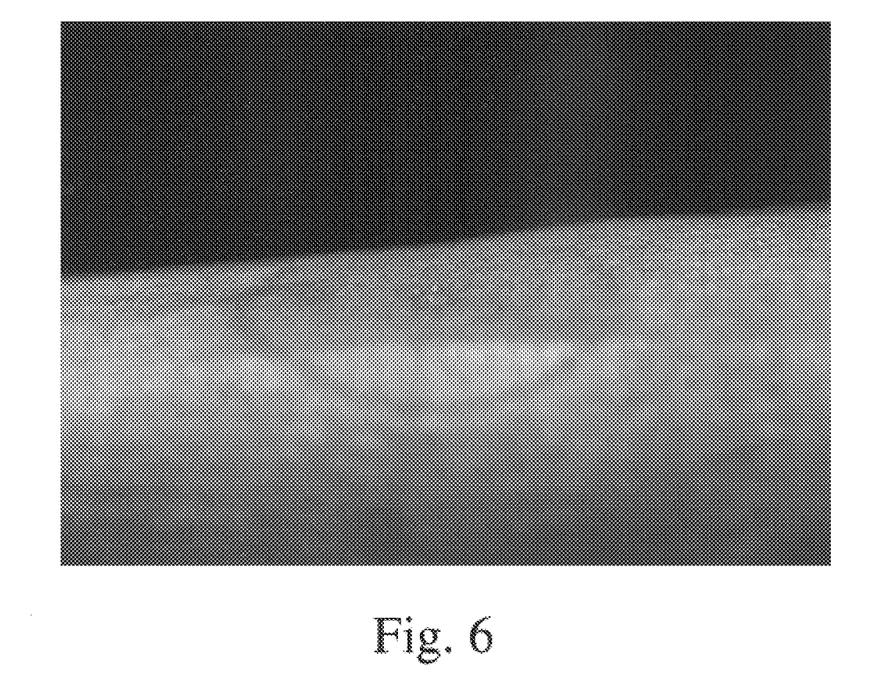
FIG. 6 shows the capsule removed and exposing the blister.
Figure 7:
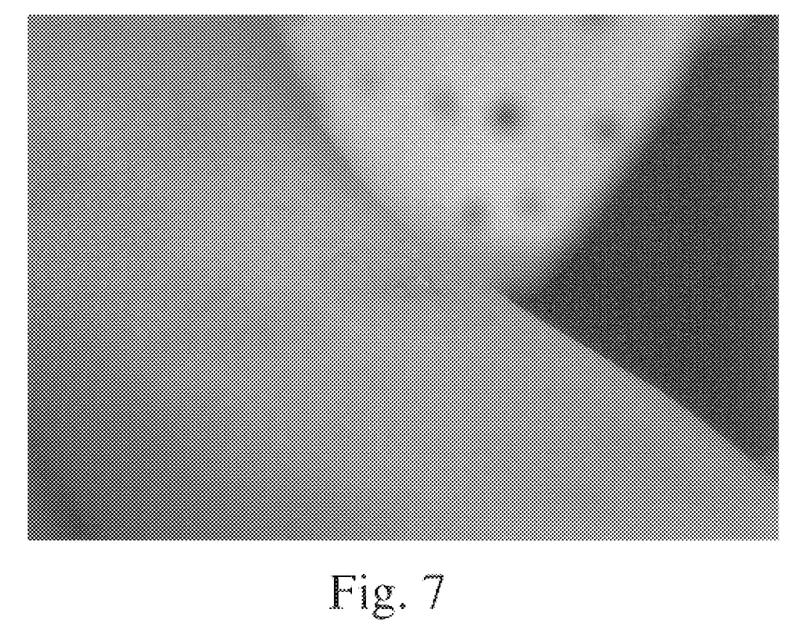
FIG. 7 shows an alternative blister formation site wherein a pair of blisters are formed side by side.
Figure 14:
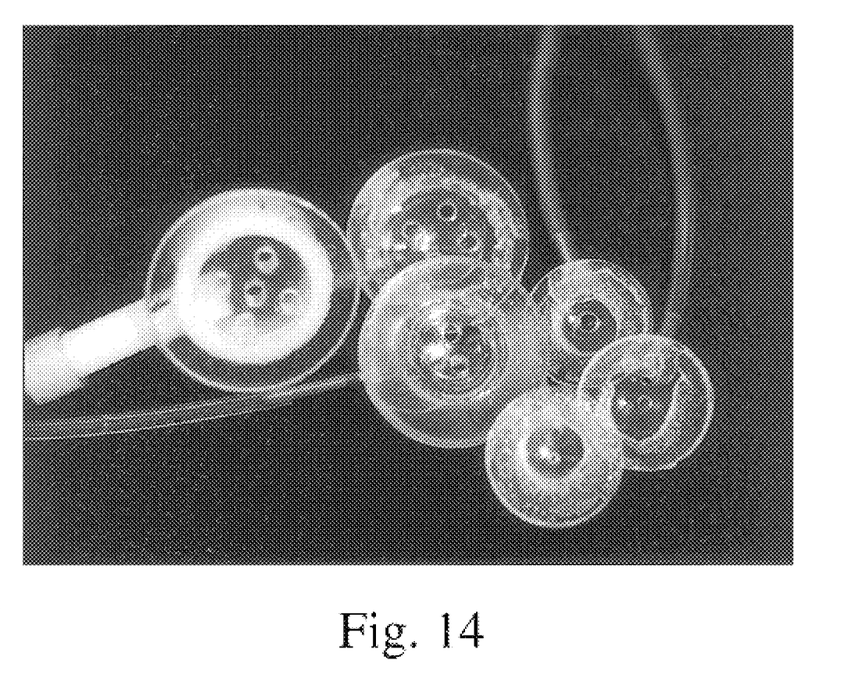
FIG. 14 shows several different embodiments of the capsule assembly.

Referring to FIGS. 1–5 and 14, the capsule consists of a chamber with connected gage, pump and appropriate valves. The gage is a pressure sensor with a digital or analog readout. Smaller pressure sensors may also be used. It and the capsule are connected to a small low level manual or electric pump. The pump creates the negative pressure that is sensed by the gage. The pump can be activated to keep the pressure at the desired level. This can vary from negative 100 to 600 mm mercury (approximately) that can be activated by the subject if and when the pressure becomes to high (less negative). The capsule is constructed of transparent synthetic material that allows the examiner to see through the capsule wall to watch for formation of a blister. Blisters are typically made in 30–120 minutes. The capsule is compact and convenient to apply so that it can be used on several sites simultaneously for better sampling of the disease process. Because of the time required to form a blister the small capsule design permits the subject to be free to move about or even leave to go to another room and perform desired tasks.

The capsule of the present invention has several advantages over prior art capsules. The capsule is miniaturized, and uses a miniature digital gauge, tubing and pumps. Several can be applied for sampling skin at distant skin sites. The miniaturization makes the capsule useful-for many skin areas that the other capsules will not fit onto. It makes it possible to do multiple separated sites with relative ease. The materials are inexpensive making the devise disposable for patient protection.

The descriptions above and the accompanying drawings should be interpreted in the illustrative and not the limited sense. While the invention has been disclosed in connection with the preferred embodiment or embodiments thereof, it should be understood that there may be other embodiments which fall within the scope of the invention.

What is claimed is:

1. A method of isolating epidermal nerves for evaluation, comprising the steps of:
   (a) forming a blister on the skin of a subject to isolate epidermal nerve fibers in a blister roof formed by the epidermis of the subject; and
   (b) removing the blister roof from the skin of the subject for evaluation of the isolated epidermal nerves.

2. The method of isolating epidermal nerves for evaluation of claim 1, wherein the step of forming a blister includes the steps of:
   (a) applying a predetermined amount of negative pressure to a predetermined area of the skin;
   (b) maintaining the predetermined amount of negative pressure for a predetermined amount of time; and
   (c) removing the predetermined amount of negative pressure.

3. The method of isolating epidermal nerves for evaluation of claim 2, wherein the step of applying negative pressure includes the steps of:
   (a) applying a capsule against the skin of the subject;
   (b) attaching a first end of a tube to a stem of the capsule;
   (c) attaching a pump to a second end of the tube; and
   (d) actuating the pump to create a desired negative pressure within the tube and within one or more holes in the capsule, the negative pressure in the capsule drawing the skin into the one or more holes.

4. The method of isolating epidermal nerves for evaluation of claim 2, wherein the step of maintaining the predetermined amount of negative pressure includes the steps of monitoring a pressure gauge on the pump and manually adjusting the pump.

5. The method of isolating epidermal nerves for evaluation of claim 2, wherein the step of maintaining the predetermined amount of negative pressure includes the step of clamping the tube closed.

6. The method of isolating epidermal nerves for evaluation of claim 1, wherein the step of removing the blister roof includes the steps of cutting the blister roof from the epidermal tissue surrounding the blister and storing the blister roof as a sample of the epidermis and associated epidermal nerves.

7. The method of isolating epidermal nerves for evaluation of claim 1, further including the step of heating the skin of the subject where the blister is to be formed.

8. A method of isolating epidermal nerves for evaluation, comprising the steps of:
   (a) forming a blister on the skin of a subject to isolate epidermal nerve fibers in a blister roof formed by the epidermis of the subject, wherein the step of forming the blister includes the steps of:
      (1) applying a predetermined amount of negative pressure to a predetermined area of the skin;
      (2) heating the skin of the subject where the blister is to be formed;
      (3) maintaining the predetermined amount of negative pressure for a predetermined amount of time; and
      (4) removing the predetermined amount of negative pressure; and
   (b) removing the blister roof from the skin of the subject by cutting the blister roof from the epidermal tissue surrounding the blister and storing the blister roof as a sample of the epidermis and associated epidermal nerves for evaluation of the isolated epidermal nerves.

9. A method of diagnosing neuropathy, comprising the steps of:
   (a) selecting one or more sites on the skin of a subject where it is desired to evaluate epidermal nerves;
   (b) isolating epidermal nerves for evaluation by separating and removing an epidermis sample from each selected site on the subject; and
   (c) analyzing the epidermis for epidermal nerves or epidermal nerve contents to diagnose a neuropathic condition.

10. The method of diagnosing neuropathy of claim 9, wherein said step of isolating epidermal nerves for evaluation by separating and removing an epidermis sample from the subject comprises the step of forming a blister with a blister roof, which includes the steps of:
   (a) applying a predetermined amount of negative pressure to a predetermined area of the skin;
   (b) maintaining the predetermined amount of negative pressure for a predetermined amount of time; and
   (c) removing the predetermined amount of negative pressure.

11. The method to diagnose neuropathy of claim 10, wherein the step of applying negative pressure includes the steps of:

(a) applying a capsule against the skin of the subject;

(b) attaching a first end of a tube to a stem of the capsule;

(c) attaching a pump to a second end of the tube; and (d) actuating the pump to create a desired negative pressure within the tube and within one or more holes in the capsule, the negative pressure in the capsule drawing the skin into the one or more holes.

12. The method of diagnosing neuropathy of claim 9, further including the steps of isolating the epidermal nerves again at each of the sites, and reanalyzing the epidermis for epidermal nerves or epidermal nerve contents.

13. A method of evaluating therapy for disorders of nerves, comprising the steps of:

(a) applying a therapeutic agent either systemically or locally to the skin of a patient;

(b) isolating epidermal nerves for evaluation by separating and removing an epidermis sample from each selected site on the subject; and (c) analyzing the epidermal nerves for epidermal nerve regeneration.

14. The method of evaluating therapy for disorders of nerves of claim 13, wherein said step of isolating epidermal nerves for evaluation by separating and removing an epidermis sample from the subject comprises the step of forming a blister with a blister roof, which includes the steps of:

(a) applying a predetermined amount of negative pressure to a predetermined area of the skin;

(b) maintaining the predetermined amount of negative pressure for a predetermined amount of time; and (c) removing the predetermined amount of negative pressure.

15. The method of evaluating therapy for disorders of nerves of claim 14, wherein the step of applying negative pressure includes the steps of:

(a) applying a capsule against the skin of the subject;

(b) attaching a first end of a tube to a stem of the capsule;

(c) attaching a pump to a second end of the tube; and (d) actuating the pump to create a desired negative pressure within the tube and within one or more holes in the capsule, the negative pressure in the capsule drawing the skin into the one or more holes.

16. The method of evaluating therapy for disorders of nerves of claim 14, further including the steps of extracting tissue fluid from the blister, analyzing the cellular and chemical contents of the tissue fluid or the blister roof, and evaluating the applied therapeutic agent based on the analyzed tissue fluid.

17. A method of monitoring healing in a traumatized skin area of a subject, comprising the steps of:

(a) selecting one or more monitoring sites on the traumatized skin of a subject;

(b) isolating epidermal nerves for evaluation by separating and removing an epidermis sample from each selected site on the subject; and (c) analyzing the regeneration of epidermal nerves in the epidermis sample.

18. The method of monitoring healing of claim 17, wherein said step of isolating epidermal nerves for evaluation by separating and removing an epidermis sample from the subject comprises the step of forming a blister with a blister roof, which includes the steps of:

(a) applying a predetermined amount of negative pressure to a predetermined area of the skin;

(b) maintaining the predetermined amount of negative pressure for a predetermined amount of time; and (c) removing the predetermined amount of negative pressure.

19. The method of monitoring healing of claim 18, wherein the step of applying negative pressure includes the steps of:

(a) applying a capsule against the skin of the subject;

(b) attaching a first end of a tube to a stem of the capsule;

(c) attaching a pump to a second end of the tube; and (d) actuating the pump to create a desired negative pressure within the tube and within one or more holes in the capsule, the negative pressure in the capsule drawing the skin into the one or more holes.

20. The method of monitoring healing of claim 17, further comprising the step of analyzing the regeneration of the epidermis.

21. The method of monitoring healing of claim 17, further comprising the step of analyzing the proliferation of capillaries at each selected skin site.

22. The method of monitoring healing of claim 17, further including the steps of applying a substance to the traumatized area and monitoring the response of the traumatized area.

* * * * *